US012565831B1

(12) United States Patent
Al Readean et al.

(10) Patent No.: US 12,565,831 B1
(45) Date of Patent: Mar. 3, 2026

(54) ADAPTIVE MULTI-AGENT ARCHITECTURE FOR PETROPHYSICAL DATA MANAGEMENT AND PROCESSING

(71) Applicant: Saudi Arabian Oil Company, Dhahran (SA)

(72) Inventors: Muhammad Al Readean, Dammam (SA); Abdullah Alakeely, Dhahran (SA); Amell Ali Al-Ghamdi, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 19/010,776

(22) Filed: Jan. 6, 2025

(51) Int. Cl.
| | |
|---|---|
| *E21B 47/00* | (2012.01) |
| *E21B 43/25* | (2006.01) |
| *G01N 33/24* | (2006.01) |
| *G06Q 50/02* | (2012.01) |

(52) U.S. Cl.
CPC .............. *E21B 47/00* (2013.01); *E21B 43/25* (2013.01); *G01N 33/24* (2013.01); *G06Q 50/02* (2013.01)

(58) Field of Classification Search
CPC ...... E21B 47/00; E21B 43/25; E21B 2200/20; E21B 43/00; E21B 2200/22; G01N 33/24; G06Q 50/02
See application file for complete search history.

(56) References Cited

U.S. PATENT DOCUMENTS

| | | | |
|---|---|---|---|
| 8,095,496 | B2 | 1/2012 | Gerber et al. |
| 8,121,971 | B2 | 2/2012 | Edwards et al. |
| 9,530,412 | B2 | 12/2016 | Selfridge |
| 10,334,048 | B2 | 6/2019 | Maturana et al. |
| 10,428,637 | B2 | 10/2019 | Abbassian et al. |
| 11,515,030 | B2 | 11/2022 | Mansi et al. |
| 11,774,930 | B2 | 10/2023 | Park et al. |
| 2009/0182541 | A1* | 7/2009 | Crick ...................... E21B 49/00 703/10 |
| 2014/0337429 | A1 | 11/2014 | Asenjo et al. |
| 2016/0356125 | A1* | 12/2016 | Bello ...................... G06Q 50/02 |
| 2017/0364795 | A1 | 12/2017 | Anderson et al. |
| 2018/0045031 | A1 | 2/2018 | Shaposhnikov et al. |

(Continued)

FOREIGN PATENT DOCUMENTS

| | | | | |
|---|---|---|---|---|
| AU | 2018313280 | B2 * | 9/2023 | ............... E21B 7/04 |
| BR | 102022014688 | A2 | 1/2024 | |

(Continued)

OTHER PUBLICATIONS

Israel, R. et al.; "Well Advisor—Integrating Real-time Data With Predictive Tools, Processes and Expertise to Enable More Informed Operational Decisions" (abstract only) SPE-173061-MS, SPE/IADC Drilling Conf. & Ex. London, UK,. Mar. 2015; pp. 1-6.

*Primary Examiner* — Daniel P Stephenson
(74) *Attorney, Agent, or Firm* — Bracewell LLP; Constance G. Rhebergen; Brian H. Tompkins

(57) ABSTRACT

A system and architecture for development of a hydrocarbon reservoir via automatic processing of petrophysical data using software agents. The software agents may provide data collection, quality checking, data integration, interpretation, processing, and reporting, and may be organized into six groups of functionalities: planning, acquisition, delivery, interpretation, enrichment, and reporting. The software agents may be rule-based, artificial intelligence-based, or a combination thereof.

18 Claims, 6 Drawing Sheets

(56)     References Cited

U.S. PATENT DOCUMENTS

| | | | |
|---|---|---|---|
| 2018/0321421 A1* | 11/2018 | Halabe .................. | G01V 11/00 |
| 2020/0370418 A1* | 11/2020 | Fries ....................... | E21B 47/06 |
| 2021/0109252 A1 | 4/2021 | Li | |
| 2021/0246766 A1 | 8/2021 | Wilson, III | |
| 2021/0406792 A1 | 12/2021 | Bhardwaj et al. | |
| 2022/0108026 A1 | 4/2022 | Ortiz et al. | |
| 2022/0137568 A1 | 5/2022 | Singh et al. | |
| 2022/0243575 A1* | 8/2022 | Kristensen .............. | G06F 30/28 |
| 2022/0282881 A1 | 9/2022 | Sinha et al. | |
| 2023/0055082 A1 | 2/2023 | Jandhyala et al. | |
| 2023/0203932 A1 | 6/2023 | Boone | |
| 2024/0011385 A1 | 1/2024 | Johnston et al. | |
| 2024/0044228 A1 | 2/2024 | Yerubandi et al. | |

FOREIGN PATENT DOCUMENTS

| | | | | | |
|---|---|---|---|---|---|
| CA | 3122401 A1 | * | 6/2020 | ............ | G16H 50/20 |
| CH | 714707 A1 | | 9/2019 | | |
| CN | 110130882 A | * | 8/2019 | ............ | E21B 49/00 |
| JP | 4593051 B2 | * | 12/2010 | ............ | E21B 49/00 |
| WO | 2017106021 A1 | | 6/2017 | | |
| WO | 2020139346 A1 | | 2/2020 | | |

* cited by examiner

ADAPTIVE MULTI-AGENT ARCHITECTURE FOR PETROPHYSICAL DATA MANAGEMENT AND PROCESSING

BACKGROUND

Field of the Disclosure

The present disclosure generally relates to the extraction of hydrocarbon (for example, oil and gas) resources from a hydrocarbon reservoir. More specifically, embodiments of the disclosure relate to the development of the hydrocarbon reservoir via management and evaluation of petrophysical data.

Description of the Related Art

The extraction of hydrocarbon resources from reservoirs in rock formations may depend on a variety of factors. In some instances, obtaining, managing, and evaluating information (referred to as "petrophysical data") about a hydrocarbon reservoir and the associated operations may be difficult due to the different types of reservoirs and operations and the amount and detail of the information. The information is typically managed by multiple personnel at various stages of development of a reservoir. However, managing and understanding the petrophysical data is difficult and may lead to suboptimal operations and inefficient extraction of hydrocarbons from a reservoir.

SUMMARY

Managing petrophysical data is a multi-stage and time-consuming process. Existing techniques require human intervention at each stage. Moreover, the handling of vast amounts of data is challenging for humans to grasp, especially regarding the potential impact of changes in interpretation parameters and models due to the availability of new petrophysical data.

In one embodiment, a method of developing a hydrocarbon reservoir using petrophysical data obtained from lab analysis or from a well logging tool inserted into a well accessing a formation containing the hydrocarbon reservoir and a plurality of agents arranged into a plurality of groups, each group having at least one agent of the plurality of agents executing on a data processing system. The method includes determining, via a first group of the plurality of groups, a plan for conducting a well logging operation or a lab analysis to generate the petrophysical data, determining, via a second group of the plurality of groups, acquisition of the petrophysical data within a time period, and validating, via a third group of the plurality of groups, the acquired petrophysical data. The method also includes interpreting, via a fourth group of the plurality of groups, the validated petrophysical data to produce petrophysical evaluation data and performing a well operation based on the petrophysical evaluation data.

In some embodiments, the method includes conducting a well logging operation based on the plan for conducting a well logging operation. In some embodiments, the plurality of agents are a plurality of rule-based agents, a plurality of AI-based agents, or a combination thereof. In some embodiments, the method includes determining, via a fifth group of the plurality of groups, a path for the well using interpreted petrophysical data, a health of the well using the interpreted well log data, or a rock type for the formation using the interpreted petrophysical data, and determining, via a sixth group of the plurality of groups a key performance indicator (KPI) and operational status of the plurality of agents. In some embodiments, the well logging data is pulsed neutron (PN) logging data, nuclear magnetic resonance (NMR) logging data, resistivity logging data, formation testing data, production logging data, integrity logging data, acoustic logging data, bulk density logging data, compensated neutron-porosity (CNL) logging data, dielectric logging data or any combination thereof. In some embodiments, the well operation is a well stimulation operation or a well completion operation. In some embodiments, determining, via a first group of the plurality of groups, the plan for conducting a well logging operation or a lab analysis includes obtaining drilling data and logging job data for offset wells, generating the plan for conducting the well logging operation or the lab analysis, determining that the agent does not need user input, and providing a notification with the plan for conducting the well logging operation or the lab analysis.

In some embodiments, a non-transitory computer-readable storage medium is provided having executable code stored thereon for developing a hydrocarbon reservoir using petrophysical data obtained from lab analysis or from a well logging tool inserted into a well accessing a formation containing the hydrocarbon reservoir and a plurality of agents arranged into a plurality of groups, each group having at least one agent of the plurality of agents executing on a data processing system. The executable code has a set of instructions that causes a processor to perform operations that include determining, via a first group of the plurality of groups, a plan for conducting a well logging operation or a lab analysis to generate the petrophysical data, determining, via a second group of the plurality of groups, acquisition of the petrophysical data within a time period, and validating, via a third group of the plurality of groups, the acquired petrophysical data. The operations also include interpreting, via a fourth group of the plurality of groups, the validated petrophysical data to produce petrophysical evaluation data and performing a well operation based on the petrophysical evaluation data.

In some embodiments, the operations include conducting a well logging operation based on the plan for conducting a well logging operation. In some embodiments, the plurality of agents are a plurality of rule-based agents, a plurality of AI-based agents, or a combination thereof. In some embodiments, the operations include determining, via a fifth group of the plurality of groups, a path for the well using interpreted petrophysical data, a health of the well using the interpreted well log data, or a rock type for the formation using the interpreted petrophysical data, and determining, via a sixth group of the plurality of groups a key performance indicator (KPI) and operational status of the plurality of agents. In some embodiments, the well logging data is pulsed neutron (PN) logging data, nuclear magnetic resonance (NMR) logging data, resistivity logging data, formation testing data, production logging data, integrity logging data, acoustic logging data, bulk density logging data, compensated neutron-porosity (CNL) logging data, dielectric logging data or any combination thereof. In some embodiments, the well operation is a well stimulation operation or a well completion operation. In some embodiments, determining, via a first group of the plurality of groups, the plan for conducting a well logging operation or a lab analysis includes obtaining drilling data and logging job data for offset wells, generating the plan for conducting the well logging operation or the lab analysis, determining that the agent does not need user input, and providing a notification with the plan for conducting the well logging operation or the lab analysis.

In another embodiment, a system is provided for of developing a hydrocarbon reservoir using petrophysical data obtained from lab analysis or from a well logging tool inserted into a well accessing a formation containing the hydrocarbon reservoir and a plurality of agents arranged into a plurality of groups, each group having at least one agent of the plurality of agents executing on the system. The system includes a processor and a non-transitory computer-readable memory accessible by the processor and having executable code stored thereon. The executable code includes a set of instructions that causes a processor to perform operations that include determining, via a first group of the plurality of groups, a plan for conducting a well logging operation or a lab analysis to generate the petro-physical data, determining, via a second group of the plurality of groups, acquisition of the petrophysical data within a time period, and validating, via a third group of the plurality of groups, the acquired petrophysical data. The operations also include interpreting, via a fourth group of the plurality of groups, the validated petrophysical data to produce petrophysical evaluation data and performing a well operation based on the petrophysical evaluation data.

In In some embodiments, the plurality of agents are a plurality of rule-based agents, a plurality of AI-based agents, or a combination thereof. In some embodiments, the operations include determining, via a fifth group of the plurality of groups, a path for the well using interpreted petrophysical data, a health of the well using the interpreted well log data, or a rock type for the formation using the interpreted petrophysical data, and determining, via a sixth group of the plurality of groups a key performance indicator (KPI) and operational status of the plurality of agents. In some embodiments, the well logging data is pulsed neutron (PN) logging data, nuclear magnetic resonance (NMR) logging data, resistivity logging data, formation testing data, production logging data, integrity logging data, acoustic logging data, bulk density logging data, compensated neutron-porosity (CNL) logging data, dielectric logging data or any combination thereof. In some embodiments, the well operation is a well stimulation operation or a well completion operation. In some embodiments, determining, via a first group of the plurality of groups, the plan for conducting a well logging operation or a lab analysis includes obtaining drilling data and logging job data for offset wells, generating the plan for conducting the well logging operation or the lab analysis, determining that the agent does not need user input, and providing a notification with the plan for conducting the well logging operation or the lab analysis.

DETAILED DESCRIPTION

The present disclosure will be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

Embodiments of the disclosure are directed to a system and architecture for development of a hydrocarbon reservoir via automatic processing of petrophysical data (such as data obtained from lab analysis or well logging operations) using software agents. The software agents may provide data collection, quality checking, data integration, interpretation, processing, and reporting, and may be organized into six groups of functionalities: planning, acquisition, delivery, interpretation, enrichment, and reporting. The software agents may operate may be rule-based, artificial intelligence-based, or a combination thereof.

Figure 1:
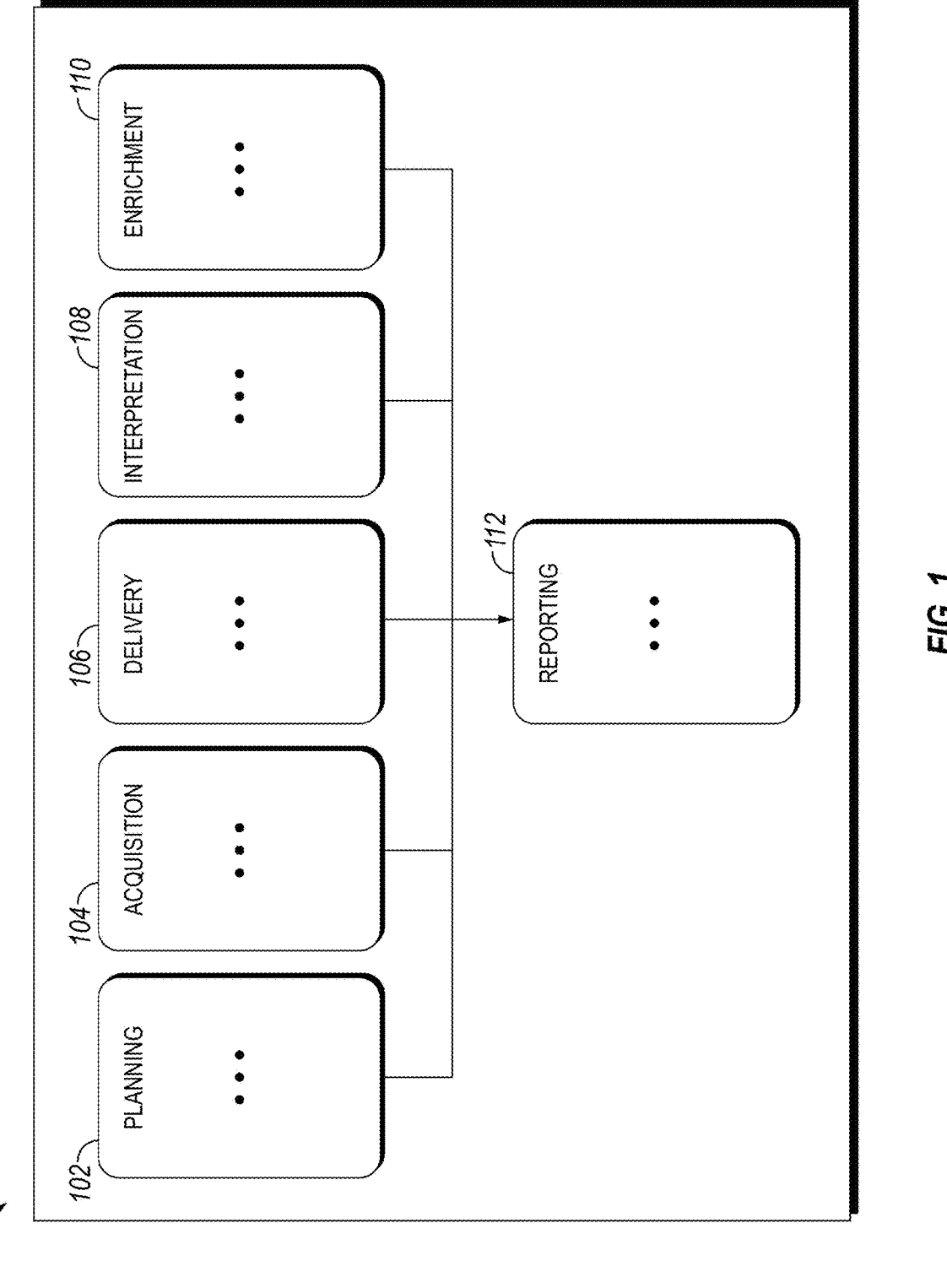
FIG. 1 is a block diagram of an overview of a multi-agent architecture for petrophysical data in accordance with an embodiment of the disclosure.

FIG. 1 depicts an overview of a multi-agent architecture 100 for petrophysical data in accordance with an embodiment of the disclosure. As shown in FIG. 1, the architecture includes a planning group 102, an acquisition group 104, a delivery group 106, an interpretation group 108, an enrichment group 110, and a reporting group 112. As disclosed in the disclosure, each group may include one or more agents that operate together to provide an output to other agents in other groups.

As described in the disclosure, the agents may each be a software module implementing a ruled-based mode, an artificial intelligence (AI) based mode, or a combination thereof. For example, an agent may obtain and process data according to a rule-based logic, such as an expert system or AI-based logic. The AI-based logic may include, for example, fuzzy logic, machine learning or artificial neural networks.

The planning group 102 may facilitate activities related to planning a logging job or lab analysis using available information such as planned well information (for example, location, drilling plan, target formation, and so on). and offset well details. The acquisition group 104 may monitor field operations, lab analysis, or both to ensure data acquisition and submission are performed within a specific time period. The delivery group 106 may validate the data quality of the delivered petrophysical data. The interpretation group 108 may include processes for the analysis and translation of the petrophysical data. The interpretation may include determining porosity, water saturation, mineral composition, and volumes from the petrophysical data. The enrichment group 110 defines the scope of functionalities for decision making by providing intelligent actionable insights through different agents. Finally, the reporting group 112 monitors all agent processes and provides key performance indicators (KPIs)

and status about ongoing operations in addition to visual or textual reporting of data throughout the system.

Figure 2:
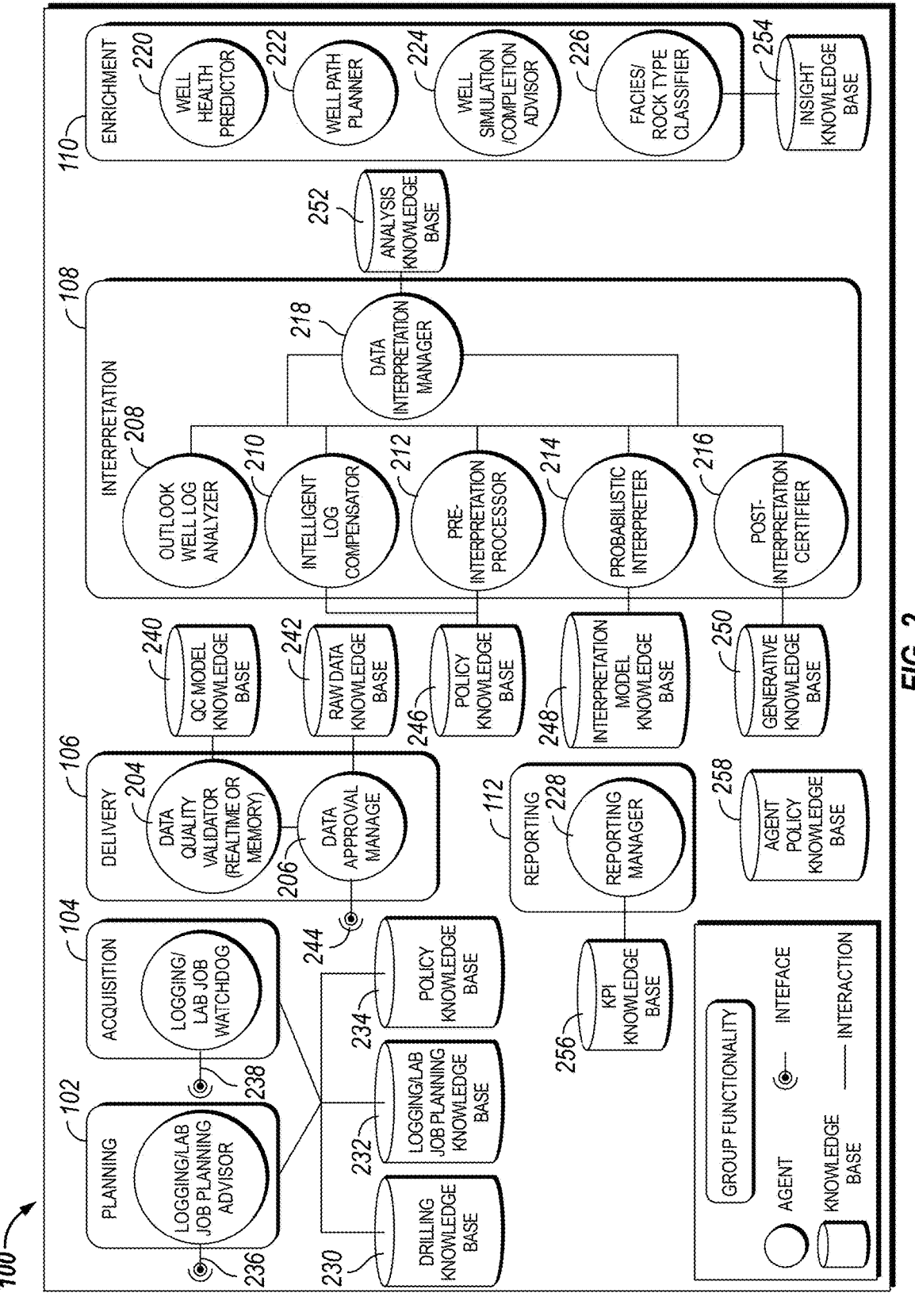
FIG. 2 is a detailed schematic diagram of the multi-agent architecture of FIG. 1 in accordance with an embodiment of the disclosure.

FIG. 2 is a detailed schematic diagram of the multi-agent architecture 100 in accordance with an embodiment of the disclosure. FIG. 2 depicts the agents within each group 102, 104, 106, 108, 110, and 112, as well as the different knowledge bases, interactions, and interfaces. As used herein, "interfaces" refer to hardware, software or both that provide two-way channel of communication with external entities/systems, such as direct graphical user interface with minimal input (for example, for action acceptance) or other external system to track external events (for example, logging operations).

As shown in FIG. 2, the planning group 102 includes a logging/lab job planning advisor agent 200, the acquisition group 104 includes a logging/lab job watchdog agent 202, and the delivery group 106 includes a data quality validator agent 204 and a data approval manager 206. As used herein the term "logging/lab" refers to data or operations involving logging data, lab data, or a combination thereof. As also shown in FIG. 2, the interpretation group 108 includes the following agents: quicklook well log analyzer 208, intelligent log compensator 210, pre-interpretation processor 212, probabilistic interpreter 214, post-interpretation certifier 216, and data interpretation manager 218. The enrichment group 110 shown in FIG. 2 includes the following agents: a well health predictor 220, a well path planner 222, a well stimulation and completion agent 224, and a facies/rock type classifier 226. The reporting group 112 includes a reporting manager agent 228.

As shown in FIG. 2, the agents of the planning group 102 and the acquisition group 104 may obtain information from a drilling knowledge base 230, a logging/lab job planning knowledge base 232, and an agent policy knowledge base 232. A knowledge base as depicted in FIG. 2 and discussed herein may be a computer-readable structured data set (for example, a database).

Figure 3:
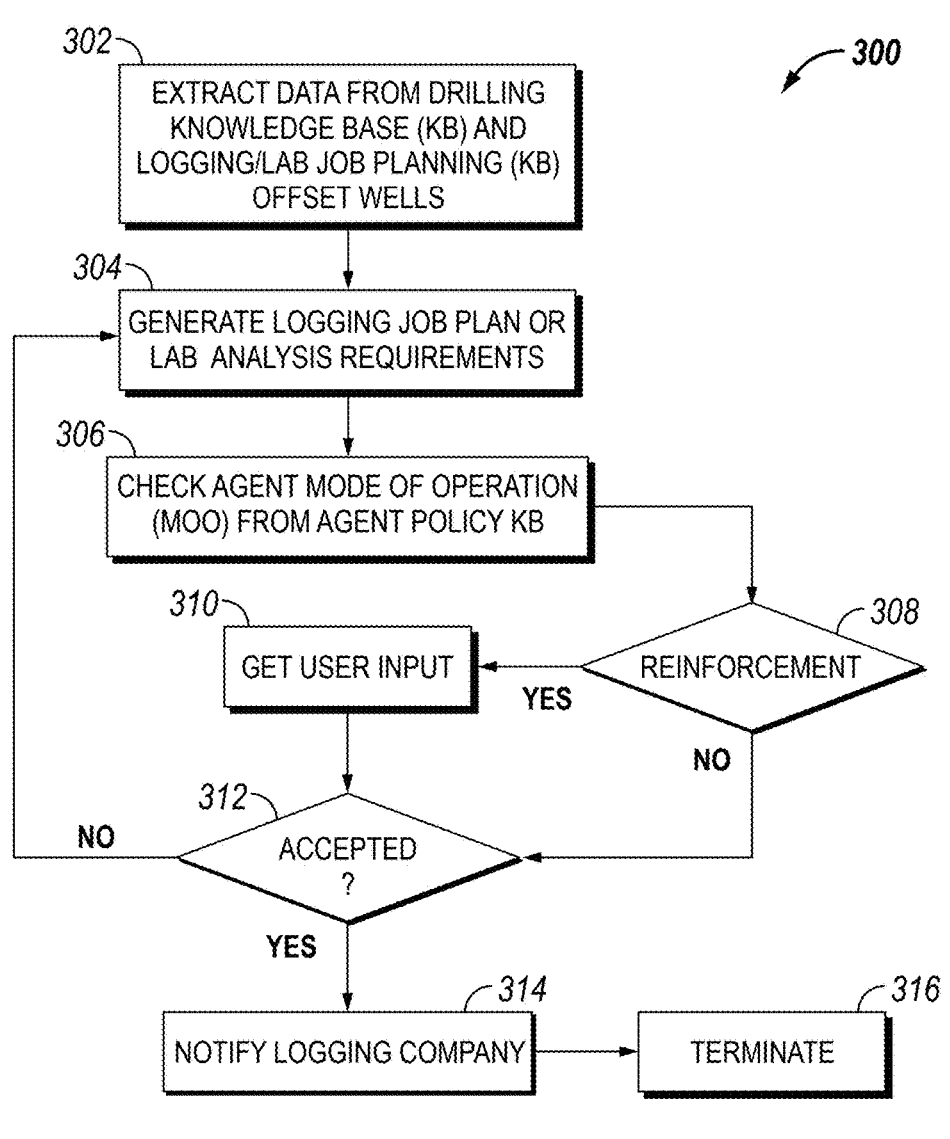
FIG. 3 is a flowchart of a process showing operation of a logging/lab job planning advisor agent in accordance with an embodiment of the disclosure.

The planning group 102 may include or have access to an interface 234 for obtaining inputs from external entities. The logging/lab job planning advisor agent 200 may obtain well information via the interface 234 and generate a well logging job plan. By way of example, FIG. 3 depicts a process 300 showing operation of the logging job planning advisor 202 in accordance with an embodiment of the disclosure. Initially, the data may be extracted from the drilling knowledge base 230 and the logging/lab job planning knowledge base 232 (block 302). Next, a logging job plan or lab analysis requirements may be generated (block 304). The agent mode of operation (MOO) may be verified using the agent policy knowledge base 232 (block 306) to determine if the agent needs reinforcement (decision block 308). If the agent needs reinforcement, user input may be requested (block 310) before proceeding to acceptance of the logging job plan or lab analysis requirements (decision block 312). If the agent does not need reinforcement, the logging job plan or lab analysis requirements is directly provided for acceptance (decision block 312).

If the logging job plan or lab analysis requirements are accepted, a logging company or lab may be notified (block 314) so that logging may proceed, after which the process 300 terminated (block 316). The logging company may include performing a well logging operation in a well via, for example, a wireline logging operation, logging-while-drilling (LWD), or other operations. If the logging job plan or lab analysis requirements are not accepted, the process 300 may return to the generation of another logging job plan or lab analysis requirements (block 304).

Figure 4:
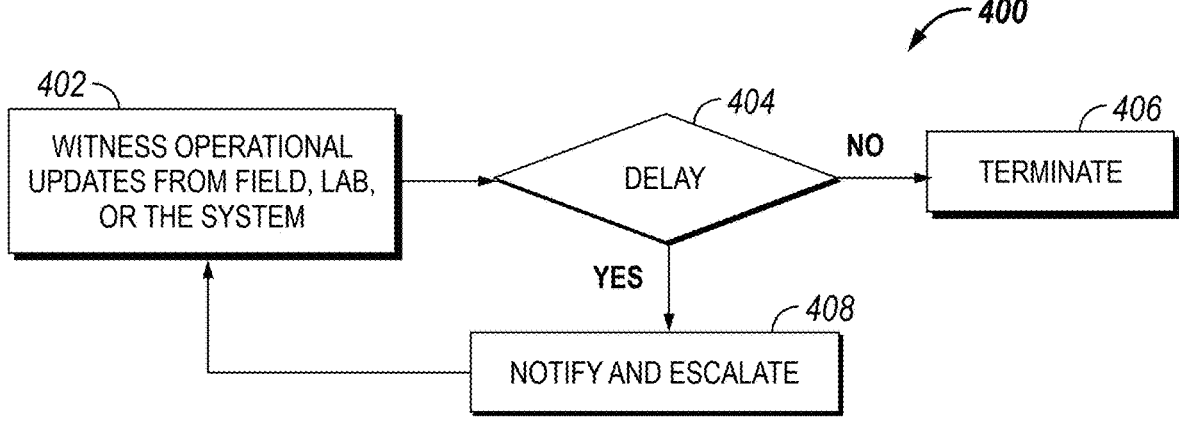
FIG. 4 is a flowchart of a process showing operation of a logging/lab job watchdog in accordance with an embodiment of the disclosure.

The agents of the acquisition group 104 may monitor operations to ensure new logging or lab analysis data is acquired as it is generated. The acquisition group 104 may include or have access to an interface 238 for obtaining inputs relating to a well and potential well logging operation or lab analysis. The logging/lab job watchdog 202 of the acquisition group 104 may monitor the execution of a logging job to ensure data is available within a minimum time period. The logging/lab job watchdog 202 may respond to changes in the environment. For example, the logging/lab job watchdog 202 may respond to a delay in data by notifying personnel and escalating the delay. By way of example, FIG. 4 depicts a process 400 showing operation of the logging/lab job watchdog 202 in accordance with an embodiment of the disclosure. As shown in FIG. 4, the logging/lab job watchdog 202 may obtain operational updates from the field, from a lab, or from a system, regarding the availability of data (block 402). The availability of the data may be evaluated to determine if there is a delay in the availability (decision block 404). If there is no delay, the process terminates (block 406) and no notification is required (block 406). If there is a delay, a notification and escalation may be performed (block 408) to ensure that the appropriate personnel are aware of and can address the delay in data acquisition.

Figure 5:
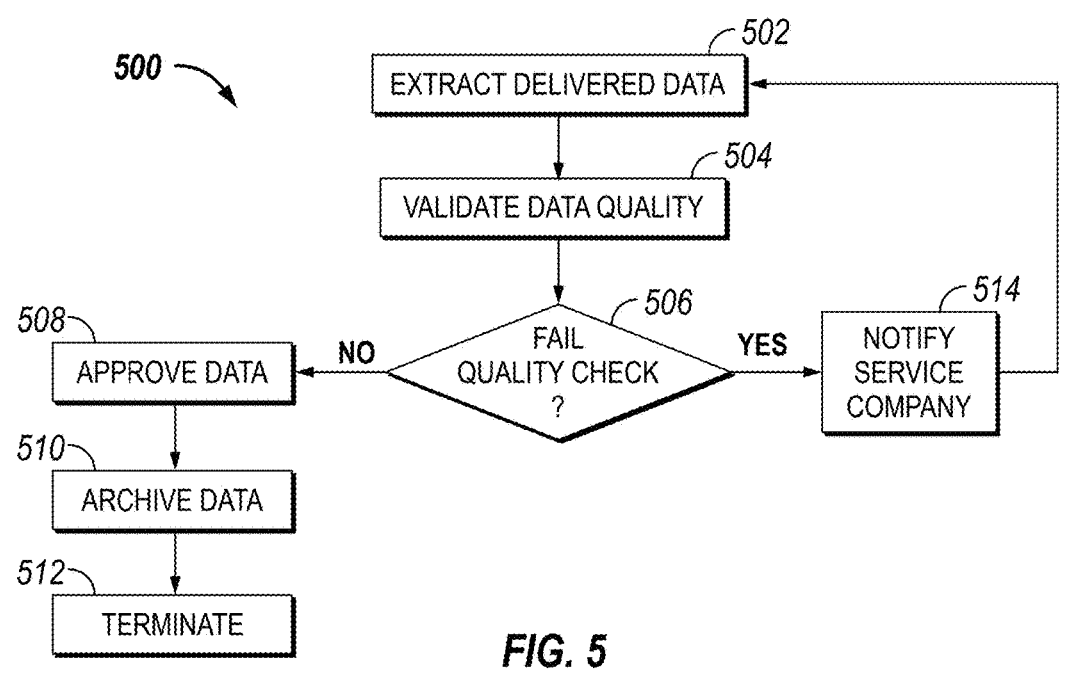
FIG. 5 is a flowchart of a process showing operation of a data quality validator agent and the data approval manager agent in accordance with an embodiment of the disclosure.

The agents of the delivery group 106 may ensure acquired data is suitable for delivery for analysis and interpretation. As shown in FIG. 2, the agents of the delivery group 106 may obtain information from a quality control (QC) knowledge base 240 and a raw data knowledge base 242. The delivery group 106 may include or have access to an interface 244 for obtaining inputs relating to a well and potential well logging operation. The data quality validator agent 204 may evaluate well logging or lab data to ensure the data is valid. The data approval manager 206 may approve (or not approve) the well logging data or lab analysis data after the validation. Each of the agents of the delivery group 106 may respond to changes in the environment. For example, data approval manager 206 may respond to a resubmission of data by requesting input. By way of example, FIG. 5 depicts a process 500 showing operation of the data quality validator agent 204 and the well log data approver 206 in accordance with an embodiment of the disclosure. Initially, delivered data may be extracted (block 502). The data quality of the delivered data is then validated (block 504) to determine whether data fails a quality check (decision block 506). If the data does not fail the quality check, the data may be approved (block 508), after which the data is then archived (block 510) and the process ends (block 512). If the data fails the quality check, a service company is notified (block 514). The process then continues with extraction of the delivered data (block 502).

As also shown in FIG. 2, the agents of the interpretation group 108 may obtain information from a policy knowledge base 246, an interpretation model knowledge base 248, and a generative knowledge base 250. The quicklook well log analyzer 208 may provide a "quicklook" analysis of well log data as is known in the art. A "quicklook" analysis may include interpreting logging data (for example, logging while drilling (LWD) data) to estimate petrophysical properties, such as lithology, porosity, fluid saturation, etc. The intelligent log compensator 210 may compensate for missing data or logs.

The pre-interpretation processor 212 may prepare the data in format suitable for later interpretation by ensuring standard naming and sampling rate or performing environmental corrections or depth shifting data, etc. In addition, pre-interpretation processor takes care of core lab measurements integration. The probabilistic interpreter 214 may provide a probabilistic interpretation of well log data depending on the data type. In the probabilistic interpretation, mineral volumes are estimated as a function of well log responses for conventional well logs. The solution may be calibrated against other data. The post-interpretation certifier 216 may certify petrophysical evaluation data. The certification ensures both the right model and parameters are used to interpret data, confirming that the interpretation is consistent with regional understanding of the geological area.

Figure 6:
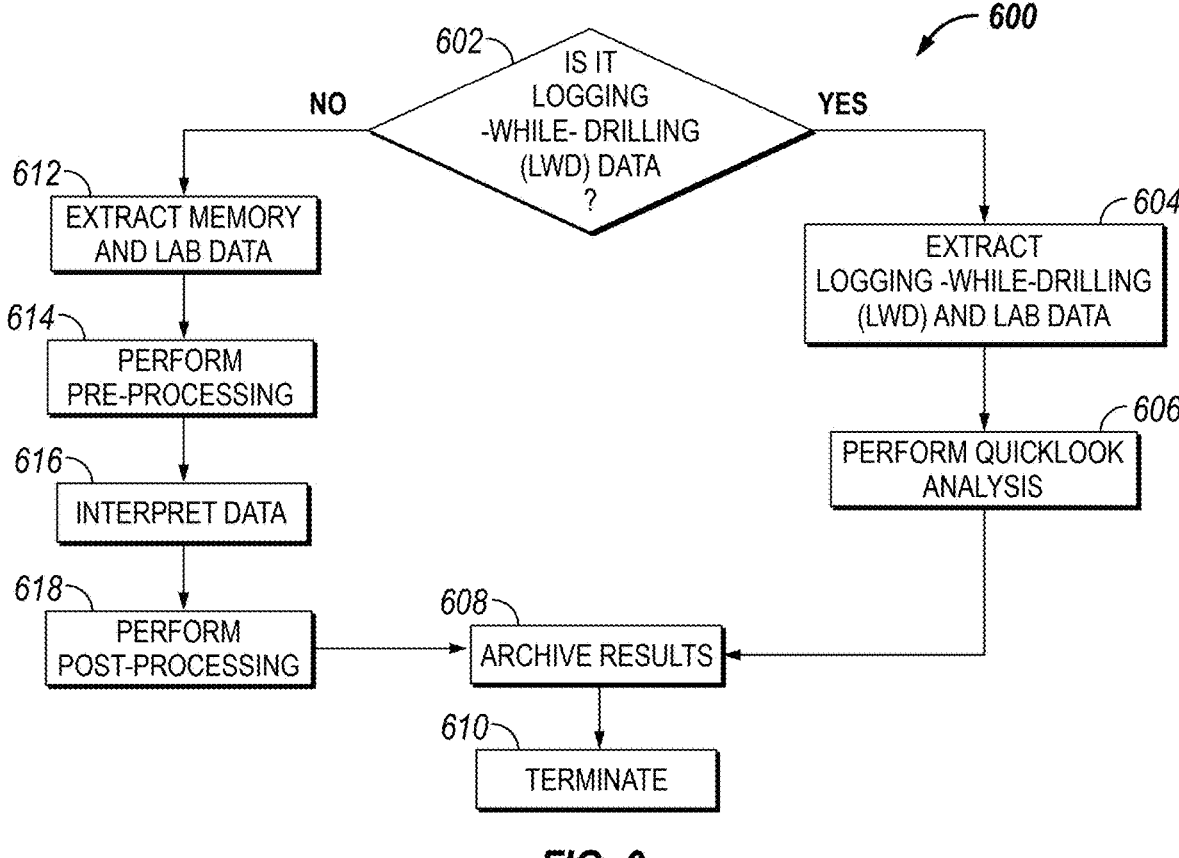
FIG. 6 is a flowchart of a process showing operation of agents of an interpretation group in accordance with an embodiment of the disclosure.

Finally, the data interpretation manager 218 may manage each of the other agents of the interpretation group 108 to ensure that each agent acts at the appropriate step, and receives inputs from and outputs data to any other agents. For example, FIG. 6 depicts a process 600 depicting operation of the agents of the interpretation group 108 in accordance with an embodiment of the disclosure. Initially, the availability of logging-while-drilling (LWD) data is determined (decision block 602). If the data type is logging-while-drilling (LWD) data, the logging-while-drilling (LWD) data and lab data may be extracted (block 604). The extracted logging-while-drilling (LWD) data and lab data may undergo a quicklook analysis (block 606). The results of the analysis are then archived (block 608) and the process terminates (block 610).

If the data type is not logging-while-drilling (LWD) data, the memory and lab data may be extracted (block 612). The data may undergo preprocessing (block 614). Next, the preprocessed data may be interpreted (block 616). The interpreted data (also referred to as "petrophysical evaluation data") may undergo postprocessing (block 618). The postprocessed data is then archived (block 608) and the process terminates (block 610).

In some embodiments, the data output from the interpretation group 108 may be used to select and perform well operations for a well. In some embodiments a well logging operation may be performed based on the interpreted data. For example, the interpreted data may indicate additional or incomplete well log data that needs to be supplemented with additional well logging data. In some embodiments, an additional well may be drilled based on the interpreted data, such as by drilling the well using a drill string and a drill bit along a well path partially based on the interpreted data. For example, the interpreted data may indicate the location or presence of additional hydrocarbons accessible by another well.

Additionally, as shown in FIG. 2, the agents of the enrichment group may obtain information from an insight knowledge base 254. The agents of the enrichment group may extract insights from interpreted well logs to provide outputs such as well health predictions, well path planning, stimulation recommendations, and reservoir characterization. For example, the well health prediction agent may analyze the interpreted well log data and make a determination of the health of the well. The well path planner agent may determine an optimal well path plan based on the interpreted well log data of offset wells. The well stimulation/completion advisor may provide recommendations for well stimulation or completion operations based on the well log data. The facies/rock type classifier may provide a classification of facies/rock types at depths within a well based on the interpreted well log data.

Finally, the reporting group 112 may monitor all actions performed by other agents in the system. Additionally, using a KPI Knowledge Base 256, the reporting group may provide information about Key Performance Indicators (KPIs) relating to the business and the involved agents and may provide visual and textual view of the data at different stages of processing and analysis. For example, a metric on the quality of the pre-interpretation processing and the post-interpretation certifier may be KPIs about the agents themselves. In another example, the number of delivered jobs vs planned ones or turnaround time may be examples of business KPIS Additionally, as shown in FIG. 2, the multi-agent architecture 100 may include an agent policy knowledge base 258 that may store the policies for the agents of the multi-agent architecture.

Each agent of the multi-agent architecture 100 may respond to changes in the well logging environment. For example, the data quality validator agent 204 of the delivery group 106 may respond to a drift in the data or in the quality control machine learning models by retraining the models. In another example, the data interpretation manager agent 218 of the interpretation group 108 may respond to a change of the processing model by preprocessing the data. In yet another example, the intelligent log compensator 210 of the interpretation group 108 may respond to a missing log by predicting the log. In another example, the data approver manager may collect feedback from other agents to approve or reject the interpretated data and notify appropriate personnel.

Figure 7:
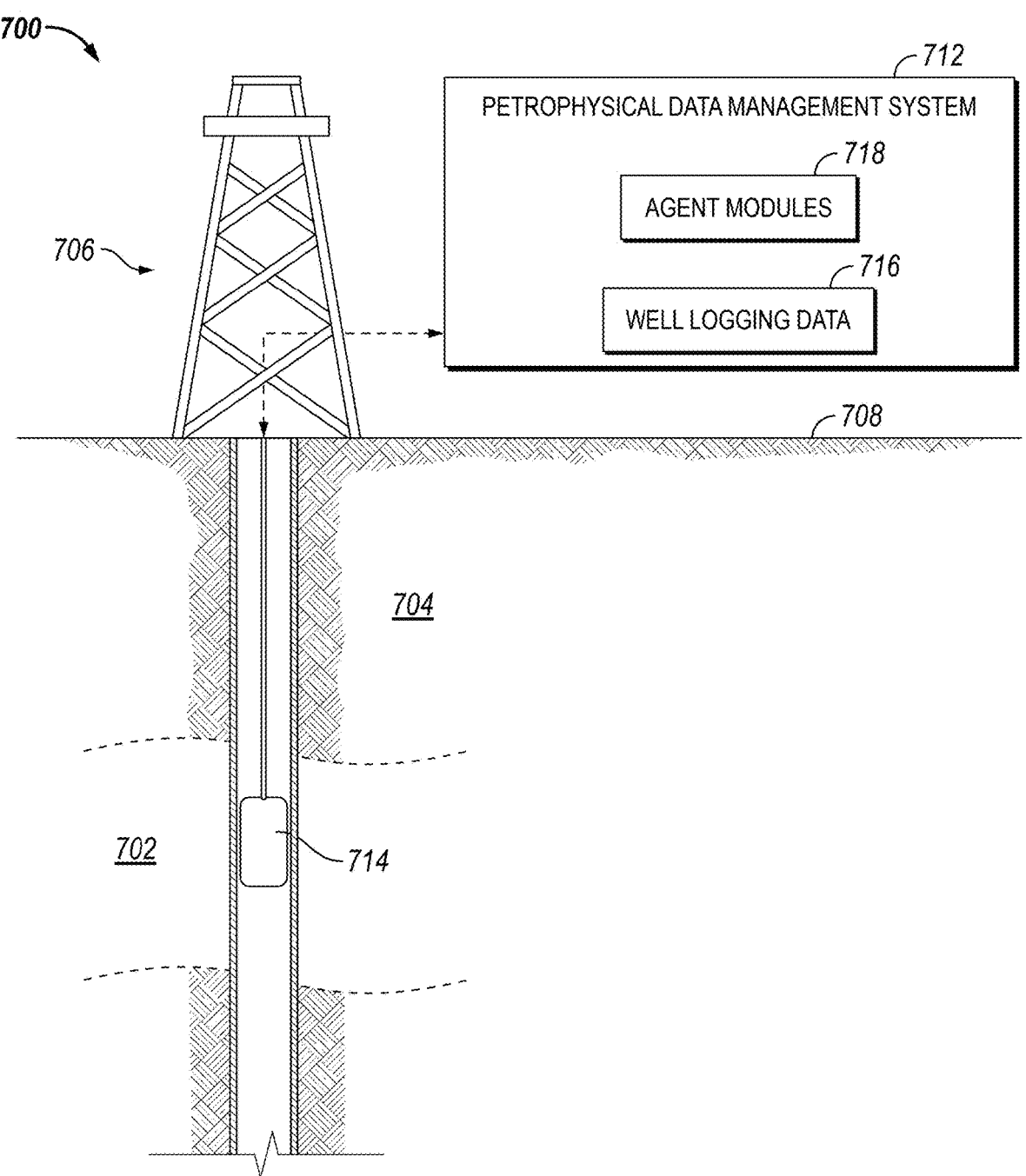
FIG. 7 is a schematic diagram of a well logging environment in accordance with an embodiment of the disclosure.

FIG. 7 is a diagram that illustrates a well logging environment 700 in accordance with one or more embodiments. In the illustrated embodiment, the well logging environment 700 includes a reservoir ("reservoir") 702 located in a subsurface formation ("formation") 704, and a well system ("well") 706.

The formation 704 may include a porous or fractured rock formation that resides underground, beneath the Earth's surface ("surface") 708. The reservoir 702 may be a hydrocarbon reservoir, and the well 706 may be a hydrocarbon well, such as an oil well. In the case of the well 706 being a hydrocarbon well, the reservoir 702 may be a hydrocarbon reservoir defined by a portion of the formation 704 that contains (or that is determined to contain or expected to contain) a subsurface pool of hydrocarbons, such as oil and gas, coexist with formation connate water. The formation 704 and the reservoir 702 may each include different layers of rock having varying characteristics, such as varying degrees of lithology, permeability, porosity, and fluid saturations. In the case of the well 706 being operated as a production well, the well 706 may facilitate the extraction of hydrocarbons (or "production") from the reservoir 702. In the case of the well 706 being operated as an injection well, the well 706 may facilitate the injection of substances, such as gas or water, into the reservoir 702. In the case of the well 706 being operated as a monitoring well, the well 706 may facilitate the monitoring of various characteristics of the formation 704 or the reservoir 702.

The well logging environment 700 may include a wellbore 710 and a petrophysical data management system 712. The petrophysical data management system 712 may control various operations of the well 706, such as well drilling operations, well completion operations, well production operations, or well and formation monitoring operations. In some embodiments, the petrophysical data management system 712 includes a computer system that is the same as or similar to that of the computer system 800 described with regard to FIG. 8.

The wellbore 710 (or "borehole") may include a bored hole that extends from the surface 708 into a target zone of the formation 704, such as the reservoir 702. An upper end of the wellbore 710, at or near the surface 708, may be referred to as the "up-hole" end of the wellbore 710. A lower end of the wellbore 710, terminating in the formation 704, may be referred to as the "downhole" end of the wellbore 710. The wellbore 710 may be created, for example, by a drill bit boring through the formation 704 and the reservoir 702. The wellbore 710 may provide for the circulation of drilling fluids during drilling operations, the flow of hydrocarbons (e.g., oil and gas) from the reservoir 702 to the surface 708 during production operations, the injection of substances (e.g., water) into the formation 704 or the reservoir 702 during injection operations, or the communication of monitoring devices (e.g., logging tools) into the formation 704 or the reservoir 702 during monitoring operations (e.g., during shut-in or flow well logging operations). In some embodiments, the wellbore 710 includes cased ("cased hole") or uncased (or "openhole") portions. A cased portion may include a portion of the wellbore 710 lined with casing (e.g., the up-hole end of the wellbore 710 may be lined with casing pipe which is cemented with the formation). An uncased portion may include a portion of the wellbore 710 that is not lined with casing (e.g., the openhole, down-hole end of the wellbore 710).

Well logging operations are conducted to measure and obtain characteristics of the reservoir and portions of the formation 704 surrounding the wellbore 710. The well logging operations may include, for example, logging-while-drilling (LWD) or measurement-while-drilling (MWD). During a well logging operation, a logging tool 714 may be lowered into the wellbore 710 and be operated to measure characteristics of the formation 704 surrounding the wellbore 710 as it is moved along a length (or "interval") of the wellbore 710. The characteristics of the formation 704 may include physical properties of the formation 704 surrounding the wellbore 710. The depth of measurement (or "investigation") into the formation 704 (e.g., the distance from the walls of the wellbore 710 into the formation 704 for which measurements are acquired) may vary based on the type and parameters of the logging operation. In some instances, the measurements are recorded in a corresponding well log that provides a mapping of the measurements versus depth in the wellbore 710. In some embodiments, the well logging operations for the well 706 are controlled by the petrophysical data management system 712 or another operator of the well 706.

The logging tool 714 and associated logging operations may include, for example, pulsed neutron (PN) logging, nuclear magnetic resonance (NMR) logging, resistivity logging, formation testing, production logging, integrity logging (for example, corrosion or cement logging) acoustic (for example, sonic) logging, bulk density logging, compensated neutron-porosity (CNL) logging, dielectric logging, or other suitable logging operations or combination thereof.

The data generated from the logging tool 714 may be provided and stored as well as logging data 716. As shown in FIG. 7, the petrophysical data management system 712 may include agent modules 718 that define the agents operating in accordance with the multi-agent architecture described herein.

Figure 8:
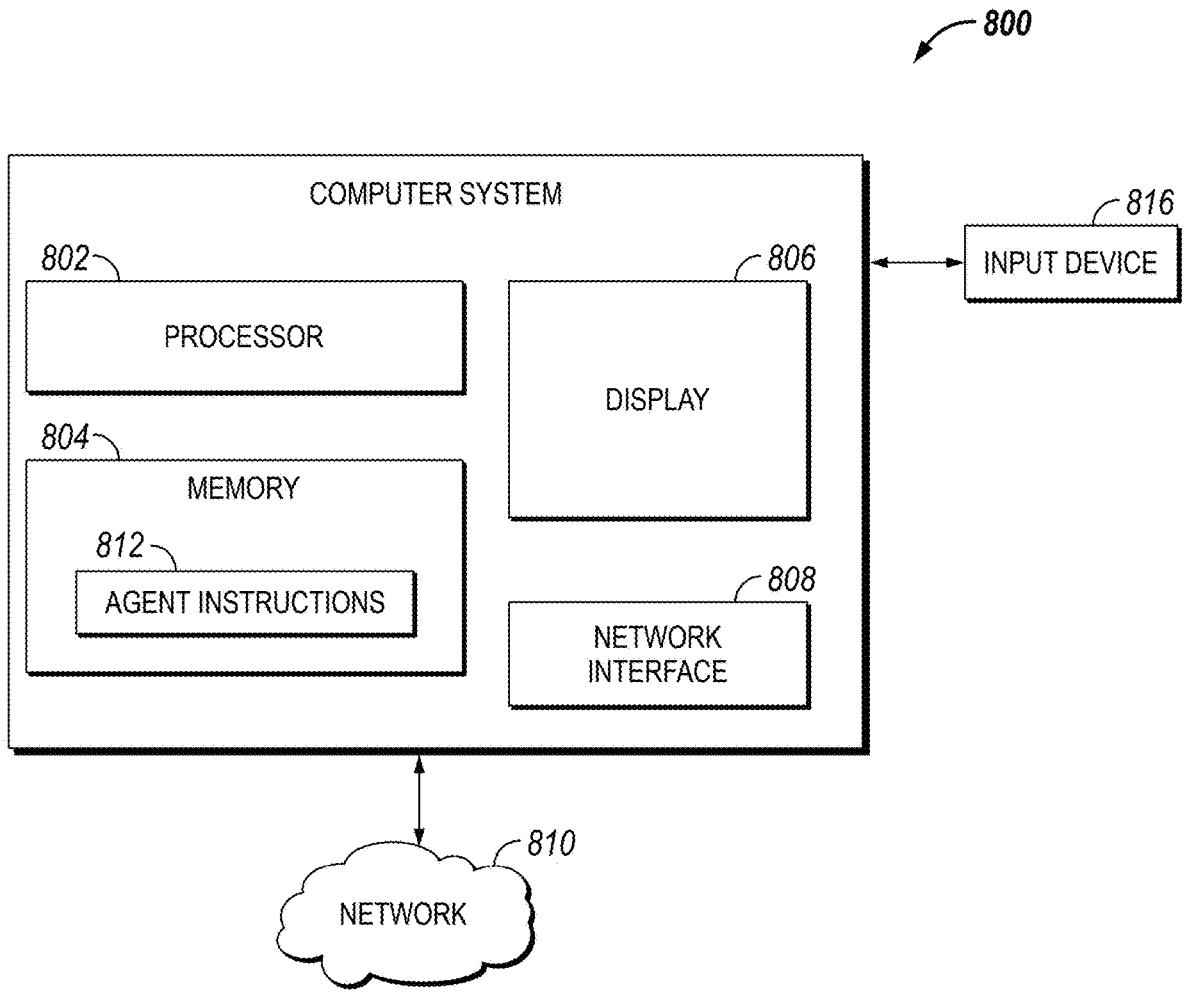
FIG. 8 is a block diagram of an example computer system in accordance with an embodiment of the disclosure.

FIG. 8 depicts components of an example computer system 800 in accordance with an embodiment of the disclosure. The example computer system 800 may represent a part of or be included with the petrophysical data management system discussed supra. In some embodiments, the example computer system 800 may be in communication with other components of a system for obtaining measurements from a well accessing a hydrocarbon-bearing reservoir. Such other components may include, for example, logging-while-drilling (LWD) systems, measurement-while-drilling (MWD) systems, and other systems that acquire information about hydrocarbon resources. As will be appreciated, such systems may use downhole tools, downhole sensors, drilling components, and other components for acquiring information about subsurface hydrocarbon resources.

As shown in FIG. 8, the example computer system 800 may include a processor 802, a memory 804, a display 806, and a network interface 808 that may be in communication with a network 810. It should be appreciated that the example computer system 800 may include other components that are omitted for clarity. In some embodiments, example computer system 800 may include or be a part of a computer cluster, cloud-computing system, a data center, a server rack or other server enclosure, a server, a virtual server, a desktop computer, a laptop computer, a tablet computer, or the like. In some embodiments, the example computer system 800 is not a part or does not have access to additional computing resources of a computer cluster, cloud computing system, etc., and may be used on-site at a remote wellsite for example.

The processor 802 (as used the disclosure, the term "processor" encompasses microprocessors) may include one or more processors having the capability to receive and process hydrocarbon resources data, such as the data described in the disclosure. In some embodiments, the processor 802 may include an application-specific integrated circuit (ASIC). In some embodiments, the processor 802 may include a reduced instruction set (RISC) processor. Additionally, the processor 802 may include a single-core processors and multicore processors and may include graphics processors. Multiple processors may be employed to provide for parallel or sequential execution of one or more of the techniques described in the disclosure. The processor 802 may receive instructions and data from a memory (for example, memory 804).

The memory 804 (which may include one or more tangible non-transitory computer readable storage mediums) may include volatile memory, such as random access memory (RAM), and non-volatile memory, such as ROM, flash memory, a hard drive, any other suitable optical, magnetic, or solid-state storage medium, or a combination thereof. The memory 804 may be accessible by the processor 802. The memory 804 may store executable computer code. The executable computer code may include computer program instructions for implementing one or more techniques described in the disclosure. For example, the executable computer code may include agent instructions 812 to implement embodiments of the present disclosure. In some embodiments, the agent instructions 812 may implement the elements of the multi-agent architecture 200 described above and illustrated in FIG. 2.

In some embodiments, the agent instructions 812 may receive, as input, data from various sources. Such sources may be or include well logs from well logging operations or lab measurements. In some embodiments, the example computer system 800 may access the data via the network 810. In some embodiments, some of the data may be manually input to the example computer system 800.

The display 806 may include a cathode ray tube (CRT) display, liquid crystal display (LCD), an organic light emitting diode (OLED) display, or other suitable display. The display 806 may display a user interface (for example, a graphical user interface) that may display information received from the example computer system 800. In accordance with some embodiments, the display 806 may be a touch screen and may include or be provided with touch sensitive elements through which a user may interact with the user interface. In some embodiments, the display 806 may display the log 814 in accordance with the techniques described herein.

The network interface 808 may provide for communication between the example computer system 800 and other devices and systems via the network 810. The network interface 808 may include a wired network interface card (NIC), a wireless (e.g., radio frequency) network interface card, or combination thereof. The network interface 808 may include circuitry for receiving and sending signals to and from communications networks, such as an antenna system, an RF transceiver, an amplifier, a tuner, an oscillator, a digital signal processor, and so forth. The network interface 808 may communicate with networks, such as the Internet, an intranet, a wide area network (WAN), a local area network (LAN), a metropolitan area network (MAN) or other networks. Communication over networks may use suitable standards, protocols, and technologies, such as Ethernet Bluetooth, Wireless Fidelity (Wi-Fi) (e.g., IEEE 802.11 standards), and other standards, protocols, and technologies. In some embodiments, for example, the log 814 may be provided to other devices over the network 810 via the network interface 808.

In some embodiments, example computer system 800 may include or be coupled to an input device 816 (for example, one or more input devices). The input devices 816 may include, for example, a mouse, a microphone, or other input devices. In some embodiments, the input device 816 may enable interaction with a user interface (for example, a graphical user interface) displayed on the display 806.

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used in the disclosure are for organizational purposes only and are not meant to be used to limit the scope of the description.

What is claimed is:

1. A method of developing a hydrocarbon reservoir using petrophysical data obtained from lab analysis or from a well logging tool inserted into a well accessing a formation containing the hydrocarbon reservoir and a plurality of agents arranged into a plurality of groups, each group comprising at least one agent of the plurality of agents executing on a data processing system, the method comprising:

determining, via a first group of the plurality of groups, a plan for conducting a well logging operation or a lab analysis to generate the petrophysical data;

determining, via a second group of the plurality of groups, acquisition of the petrophysical data within a time period;

conducting a well logging operation within the time period according to the plan for conducting a well logging operation to generate the petrophysical data;

validating, via a third group of the plurality of groups, the acquired petrophysical data;

interpreting, via a fourth group of the plurality of groups, the validated petrophysical data to produce petrophysical evaluation data;

determining, from the petrophysical evaluation data, that additional petrophysical data is required;

determining, via the first group of the plurality of groups, a second plan for conducting a second well logging operation to generate the additional petrophysical data;

conducting a second well logging operation based on the second plan to generate the additional petrophysical data;

updating the petrophysical evaluation data using the additional petrophysical data; and performing a well operation based on the petrophysical evaluation data.

2. The method of claim 1, wherein the plurality of agents comprise a plurality of rule-based agents, a plurality of AI-based agents, or a combination thereof.

3. The method of claim 1, comprising:

determining, via a fifth group of the plurality of groups, a path for the well using the petrophysical evaluation data, a health of the well using the petrophysical evaluation data, or a rock type for the formation using the petrophysical evaluation data; and determining, via a sixth group of the plurality of groups a key performance indicator (KPI) and operational status of the plurality of agents.

4. The method of claim 1, wherein the petrophysical data comprises pulsed neutron (PN) logging data, nuclear magnetic resonance (NMR) logging data, resistivity logging data, formation testing data, production logging data, integrity logging data, acoustic logging data, bulk density logging data, compensated neutron-porosity (CNL) logging data, dielectric logging data or any combination thereof.

5. The method of claim 1, wherein the well operation comprises a well stimulation operation or a well completion operation.

6. The method of claim 1, wherein determining, via a first group of the plurality of groups, the plan for conducting a well logging operation or a lab analysis comprises:

obtaining drilling data and logging job data for offset wells;

generating the plan for conducting the well logging operation or the lab analysis;

determining that the agent does not need user input; and providing a notification with the plan for conducting the well logging operation or the lab analysis.

7. A non-transitory computer-readable storage medium having executable code stored thereon of developing a hydrocarbon reservoir using petrophysical data obtained from lab analysis or from a well logging tool inserted into a well accessing a formation containing the hydrocarbon reservoir and a plurality of agents arranged into a plurality of groups, each group comprising at least one agent of the plurality of agents executing on a data processing system, the executable code comprising a set of instructions that causes a processor to perform operations comprising:

determining, via a first group of the plurality of groups, a plan for conducting a well logging operation or a lab analysis to generate the petrophysical data;

determining, via a second group of the plurality of groups, acquisition of the petrophysical data within a time period;

conducting a well logging operation within the time period according to the plan for conducting a well logging operation to generate the petrophysical data;

validating, via a third group of the plurality of groups, the acquired petrophysical data;

interpreting, via a fourth group of the plurality of groups, the validated petrophysical data to produce petrophysical evaluation data;

determining, from the petrophysical evaluation data, that additional petrophysical data is required;

determining, via the first group of the plurality of groups, a second plan for conducting a second well logging operation to generate the additional petrophysical data;

conducting a second well logging operation based on the second plan to generate the additional petrophysical data;

updating the petrophysical evaluation data using the additional petrophysical data; and controlling a well operation based on the petrophysical evaluation data.

8. The non-transitory computer-readable storage medium of claim 7, wherein the plurality of agents comprise a plurality of rule-based agents, a plurality of AI-based agents, or a combination thereof.

9. The non-transitory computer-readable storage medium of claim 7, the operations comprising:

determining, via a fifth group of the plurality of groups, a path for the well using the petrophysical evaluation data, a health of the well using the petrophysical evaluation data, or a rock type for the formation using the petrophysical evaluation data; and determining, via a sixth group of the plurality of groups a key performance indicator (KPI) and operational status of the plurality of agents.

10. The non-transitory computer-readable storage medium of claim 7, wherein the petrophysical data comprises pulsed neutron (PN) logging data, nuclear magnetic resonance (NMR) logging data, resistivity logging data, formation testing data, production logging data, integrity logging data, acoustic logging data, bulk density logging data, compensated neutron-porosity (CNL) logging data, dielectric logging data or any combination thereof.

11. The non-transitory computer-readable storage medium of claim 7, wherein the well operation comprises a well stimulation operation or a well completion operation.

12. The non-transitory computer-readable storage medium of claim 7, wherein determining, via a first group of the plurality of groups, the plan for conducting a well logging operation or a lab analysis comprises:

obtaining drilling data and logging job data for offset wells;

generating the plan for conducting the well logging operation or the lab analysis;

determining that the agent does not need user input; and providing a notification with the plan for conducting the well logging operation or the lab analysis.

13. A system for of developing a hydrocarbon reservoir using petrophysical data obtained from lab analysis or from a well logging tool inserted into a well accessing a formation containing the hydrocarbon reservoir and a plurality of agents arranged into a plurality of groups, each group comprising at least one agent of the plurality of agents executing on the system, comprising:

a processor;

a non-transitory computer-readable memory accessible by the processor and having executable code stored thereon, the executable code comprising a set of instructions that causes a processor to perform operations comprising:

determining, via a first group of the plurality of groups, a plan for conducting a well logging operation or a lab analysis to generate the petrophysical data;

determining, via a second group of the plurality of groups, acquisition of the petrophysical data within a time period;

conducting a well logging operation within the time period according to the plan for conducting a well logging operation to generate the petrophysical data;

validating, via a third group of the plurality of groups, the acquired petrophysical data;

interpreting, via a fourth group of the plurality of groups, the validated petrophysical data to produce petrophysical evaluation data; and determining, from the petrophysical evaluation data, that additional petrophysical data is required;

determining, via the first group of the plurality of groups, a second plan for conducting a second well logging operation to generate the additional petrophysical data;

conducting a second well logging operation based on the second plan to generate the additional petrophysical data;

updating the petrophysical evaluation data using the additional petrophysical data; and controlling a well operation based on the petrophysical evaluation data.

14. The system of claim 13, wherein the plurality of agents comprise a plurality of rule-based agents a plurality of AI-based agents, or a combination thereof.

15. The system of claim 13, the operations comprising:

determining, via a fifth group of the plurality of groups, a path for the well using the petrophysical evaluation data, a health of the well using the petrophysical evaluation data, or a rock type for the formation using the petrophysical evaluation data; and determining, via a sixth group of the plurality of groups a key performance indicator (KPI) and operational status of the plurality of agents.

16. The system of claim 13, wherein the petrophysical data comprises pulsed neutron (PN) logging data, nuclear magnetic resonance (NMR) logging data, resistivity logging data, formation testing data, production logging data, integrity logging data, acoustic logging data, bulk density logging data, compensated neutron-porosity (CNL) logging data, dielectric logging data or any combination thereof.

17. The system of claim 13, wherein the well operation comprises a well stimulation operation or a well completion operation.

18. The system of claim 13, wherein determining, via a first group of the plurality of groups, the plan for conducting a well logging operation or lab analysis comprises:

obtaining drilling data and logging job data for offset wells;

generating the plan for conducting the well logging operation or the lab analysis;

determining that the agent does not need user input; and providing a notification with the plan for conducting the
   well logging operation or the lab analysis.

\* \* \* \* \*